(12) United States Patent
Ishibashi et al.

(10) Patent No.: US 10,244,750 B2
(45) Date of Patent: *Apr. 2, 2019

(54) INSECT PEST-TARGETING GEL COMPOSITION AND SUSTAINED RELEASE PREPARATION COMPRISING THAT

(71) Applicant: SHIN-ETSU CHEMICAL CO., LTD., Tokyo (JP)

(72) Inventors: Naoki Ishibashi, Joetsu (JP); Ryuichi Saguchi, Joetsu (JP); Tatsuya Hojo, Joetsu (JP); Takehiko Fukumoto, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/362,242

(22) PCT Filed: Dec. 6, 2012

(86) PCT No.: PCT/JP2012/081626
§ 371 (c)(1),
(2) Date: Jun. 2, 2014

(87) PCT Pub. No.: WO2013/084982
PCT Pub. Date: Jun. 13, 2013

(65) Prior Publication Data
US 2014/0357707 A1 Dec. 4, 2014

(30) Foreign Application Priority Data
Dec. 9, 2011 (JP) ................................. 2011-270132

(51) Int. Cl.
*A01N 25/04* (2006.01)
*A01N 25/34* (2006.01)
*A01N 31/02* (2006.01)
*A01N 35/02* (2006.01)
*A01N 37/06* (2006.01)
*A01N 43/90* (2006.01)
*A01N 25/18* (2006.01)

(52) U.S. Cl.
CPC .............. *A01N 25/04* (2013.01); *A01N 25/18* (2013.01); *A01N 25/34* (2013.01); *A01N 31/02* (2013.01); *A01N 35/02* (2013.01); *A01N 37/06* (2013.01); *A01N 43/90* (2013.01)

(58) Field of Classification Search
CPC ........ A01N 25/18; A01N 27/00; A01N 35/02; A01N 37/02; A01N 43/90; A01N 25/34; A01N 31/02; A01N 25/04; A01N 37/06
See application file for complete search history.

(56) References Cited

U.S. PATENT DOCUMENTS

| | | |
|---|---|---|
| 4,353,962 A | 10/1982 | Himel et al. |
| 4,817,868 A | 4/1989 | Cook et al. |
| 6,065,687 A | 5/2000 | Suzuki et al. |
| 6,242,509 B1 | 6/2001 | Berger et al. |
| 6,372,242 B1 | 4/2002 | Gutierrez |
| 9,549,546 B2 | 1/2017 | Saguchi et al. |
| 2001/0055604 A1 | 12/2001 | Kalder et al. |
| 2005/0208085 A1* | 9/2005 | Yamato .................. A61K 8/042 424/401 |
| 2006/0093638 A1 | 5/2006 | Hojo et al. |
| 2006/0198857 A1 | 9/2006 | Casagrande |
| 2007/0148202 A1 | 6/2007 | Primo Yufera et al. |
| 2007/0248502 A1 | 10/2007 | Adair et al. |

FOREIGN PATENT DOCUMENTS

| | | |
|---|---|---|
| EP | 0160151 A2 | 11/1985 |
| EP | 0572743 A1 | 12/1993 |
| EP | 1 142 959 A1 * | 10/2001 |
| EP | 1142959 A1 | 10/2001 |
| JP | 63-222104 | 9/1988 |
| JP | 02-207002 | 8/1990 |
| JP | 02-207003 | 8/1990 |
| JP | 05-095751 | 4/1993 |
| JP | 06-255124 | 9/1994 |
| JP | 07-267809 | 10/1995 |
| JP | 11-069936 | 3/1999 |
| JP | 2001-515840 A | 9/2001 |
| JP | 2002-306584 | 10/2002 |
| JP | 2004-275010 A | 10/2004 |
| JP | 2006-124330 A | 5/2006 |
| JP | 2009-534031 A | 9/2009 |

(Continued)

OTHER PUBLICATIONS

Jadhav et al. ("Molecular gels-based controlled release devices for pheromones" in the Royal Soceity of Chemistry, (first publishes on Nov. 17, 2010), pp. 864-867).*
Office Action corresponding to Japanese Application No. 2012-265266 dated Jul. 28, 2015.
Office Action corresponding to Japanese Application No. 2012-265267 dated Jul. 28, 2015.
Office Action corresponding to Japanese Application No. 2012-265265 dated Sep. 4, 2015.
Material Data Safety Sheet for Bushman Ultra—Water Resistant Insect Repellent (2008) 6 pages.
Product Description of Bushman DryGel Insect Repellent http://web.archive.org/web/20100222095936/http://www.bushman-repellent.com/products.htm retrieved Apr. 14, 2015 (3 pages).

(Continued)

*Primary Examiner* — Blessing M Fubara
(74) *Attorney, Agent, or Firm* — Myers Bigel, P.A.

(57) ABSTRACT

Provided are an insect pest-targeting gel composition causing neither leakage nor reaction of a volatile substance and capable of releasing the volatile substance at a constant rate; and a sustained release preparation including the insect pest-targeting gel composition. More specifically, provided is an insect pest-targeting gel composition including one or more volatile substances and an oil gelling agent, wherein the volatile substance is included in an amount of from 70.0 to 99.0% by weight by the insect pest-targeting gel composition.

6 Claims, 5 Drawing Sheets

(56) References Cited

FOREIGN PATENT DOCUMENTS

| WO | WO 03/079778 A1 | 10/2003 |
|---|---|---|
| WO | WO 2004/014438 A1 | 2/2004 |
| WO | WO 2009/103991 A2 | 8/2009 |
| WO | WO 2010/088645 A2 | 8/2010 |
| WO | WO 2011/067732 A1 | 6/2011 |

OTHER PUBLICATIONS

Extended European Search Report corresponding to European Application No. 12854702.3 dated Apr. 21, 2015.
Extended European Search Report corresponding to European Application No. 12856107.3 dated Apr. 21, 2015.
Extended European Search Report corresponding to European Application No. 12856554.6 dated Apr. 22, 2015.
Patent Examination Report No. 1 corresponding to Australian Patent Application No. 2012261589 issued May 17, 2013.
International Search Report corresponding to International Application No. PCT/JP2012/081626 dated Jan. 29, 2013.
International Preliminary Report on Patentability corresponding to International Application No. PCT/JP2012/081626 mailed Jun. 10, 2014.
Examination Report corresponding to European Application No. 12854702.3 dated Jan. 19, 2018.
Examination Report corresponding to European Application No. 12856107.3 dated Jan. 19, 2018.
Examination Report corresponding to European Application No. 12856554.6 dated Jan. 17, 2018.
Patent Examination Report No. 1 corresponding to Australian Patent Application No. 2013201802 dated Sep. 25, 2013.
Heuskin et al. "The use of semiochemical slow-release devices in integrated pest management strategies", *Biotechnol. Agron. Soc. Environ.* 15(3):459-470 (2011).
International Search Report corresponding to International Application No. PCT/JP2012/081628 dated Jan. 29, 2013.
International Preliminary Report on Patentability corresponding to International Application No. PCT/JP2012/081628 dated Jun. 10, 2014.

* cited by examiner

INSECT PEST-TARGETING GEL COMPOSITION AND SUSTAINED RELEASE PREPARATION COMPRISING THAT

RELATED APPLICATIONS

This application is a 35 U.S.C. § 371 national stage application of PCT Application No. PCT/JP2012/081626, filed on Dec. 6, 2012, which claims priority from Japanese Application No. 2011-270132, filed on Dec. 9, 2011, the contents of which are incorporated herein by reference in their entireties. The above-referenced PCT International Application was published as International Publication No. WO 2013/084982 A1 on Jun. 13, 2013.

TECHNICAL FIELD

This invention relates to an insect pest-targeting gel composition and a sustained release preparation comprising the insect pest-targeting gel composition.

BACKGROUND ART

Mating disruption, emergence forecasting, mass trapping, control of insect pests in a predetermined area and the like can be accomplished by the sustained release of a pheromone substance, an attractant, a repellent or the like. As a method of sustainably releasing a volatile substance which is effective for insect pest control, over a long period of time, a method of sustainably releasing a volatile substance in liquid form, a method of sustainably releasing a volatile substance in gel form and other methods are known. For example, Patent Document 1 discloses a method comprising the steps of enclosing a volatile substance in a polymer vessel and sustainably releasing it from the polymer surface through the polymer wall; Patent Document 2 discloses a method comprising the steps of forming a volatile substance into a fluid gel and sustainably releasing the gel through a polymer film; and Patent Document 3 discloses a method comprising the steps of entrapping a volatile substance in a polymer lattice and sustainably releasing it in a solid or gel form.

PRIOR ART DOCUMENTS

Patent Documents

[Patent Document 1] JP 07-313035A11995
[Patent Document 2] JP 2002-306584A
[Patent Document 3] JP 64-055136A/1989

SUMMARY OF THE INVENTION

Problem to be Solved by the Invention

However, a preparation obtained by the method comprising the step of enclosing a volatile substance in liquid form in a polymer vessel as described in Patent Document 1 has a problem that holes or cracks are caused in the vessel as a result of rude treatment by users upon use and the volatile substance enclosed in the vessel leaks from it so that the release period is markedly decreased. The fluid gel described in Patent Document 2 also has a problem, in addition to the possibility of leakage, that a large amount of diluent has to be added to give fluidity so that the release rate of the volatile substance is decreased as the time elapses. Accordingly, there is a demand for the development of a sustained release preparation which can release a volatile substance at a constant rate without causing leakage of the volatile substance.

The polymer gel described in Patent Document 3 has no possibility of leakage of the volatile substance. However, since the gel is produced by polymerization in the presence of a volatile substance, the method cannot be applied to a volatile substance having an instable functional group which may react under polymerization conditions. Accordingly, there is a strong demand for the development of a sustained release preparation in gel form which can be produced without exposing the volatile substance to severe conditions such as polymerization conditions.

The present invention has been made with the foregoing in view. An object thereof is to provide an insect pest-targeting gel composition and a sustained release preparation comprising the insect pest-targeting gel composition, which preparation can sustainably release a volatile substance at a constant rate without causing leakage or reaction of the volatile substance.

Solution to the Problem

In order to achieve the above-mentioned object, the present inventors have studied a sustained release preparation comprising an insect pest-targeting gel composition, which preparation can sustainably and stably release a volatile substance effective for insect pest control at a given or faster rate over a long period of time. As a result, it has been unexpectedly found that the above-mentioned object is achieved by producing an insect pest-targeting gel composition and a sustained release preparation comprising the composition comprising one or more volatile substances and an oil gelling agent, wherein the one or more volatile substances are comprised in an amount of from 70.0 to 99.0% by weight by the insectpest-targeting gel composition and are released outside of a vessel through the vessel. Thus, the invention has been completed.

According to the invention, an insect pest-targeting gel composition comprising one or more volatile substances and an oil gelling agent, wherein the one or more volatile substances are comprised in an amount of from 70.0 to 99.0% by weight by the insect pest-targeting gel composition, can be provided. According to the invention, a sustained release preparation comprising a vessel having an opening portion, and the insect pest-targeting gel composition introduced into the vessel, wherein the vessel is made of a material not permitting penetration of the one or more volatile substances, can also be provided.

Effect of the Invention

According to the invention, the sustained release preparation comprising an insect pest-targeting gel composition can reduce the possibility of leakage of a volatile substance and suppress a loss of the volatile substance due to the reaction at the time of gelling because the volatile substance is gelled under mild conditions. In addition, the sustained release preparation does not contain a diluent component such as a solvent so that the release at a given or faster rate can be maintained stably for a long period of time. Furthermore, the release rate can be regulated, depending on a surface area of the gel composition; an area of the opening portion; and/or the material, thickness or the like of the polymer film. Even a volatile substance having high volatility and therefore not suited for use in conventional sustained release preparations can be released stably when used in the sustained release preparation of the invention.

EMBODIMENTS FOR CARRYING OUT THE INVENTION

The sustained release preparation of the invention comprises a polymer tube and an insect pest-targeting gel composition in the polymer tube, the composition comprising one or more volatile substances and an oil gelling agent. As a material of the polymer tube, a material which can release a volatile substance from the polymer tube to the outside through the polymer tube is used. Examples of the volatile substance to be used in the invention include a pheromone substance, an attractant, a repellent and a mixture thereof.

Examples of the pheromone substance to be used in the invention include a linear aliphatic aldehyde having from 12 to 20 carbon atoms, a linear aliphatic acetate having from 12 to 20 carbon atoms which is saturated or has one or more double bonds, a linear aliphatic alcohol having from 7 to 20 carbon atoms, a spiroacetal having from 7 to 15 carbon atoms, a linear aliphatic ketone having from 10 to 25 carbon atoms, an aliphatic hydrocarbon having from 10 to 30 carbon atoms, and a carboxylic acid having from 10 to 20 carbon atoms. Of these examples, a linear aliphatic aldehyde having from 12 to 20 carbon atoms, a linear aliphatic acetate having from 12 to 20 carbon atoms which is saturated or has one or more double bonds, a linear aliphatic alcohol having from 7 to 20 carbon atoms and a spiroacetal having from 7 to 15 carbon atoms are particularly preferred. Specific examples include Z7Z11-hexadecadienyl acetate and Z7E11-hexadecadienyl acetate which are the sex pheromone substances of the pink bollworm (*Pectinophora gossypiella*); Z-8-dodecenyl acetate which is the sex pheromone substance of the oriental fruit moth (*Grapholita molesta*); E-5-decenyl acetate which is the sex pheromone substance of the peach twig borer (*Anarsia lineatella*); Z-9-dodecenyl acetate which is the sex pheromone substance of the grape berry moth (*Eupoecilia ambiguella*); E7Z9-dodecadienyl acetate which is the sex pheromone substance of the European grape vine moth (*Lobesia botrana*); E-11-tetradecenyl acetate which is the sex pheromone substance of the light brown apple moth (*Epiphyas postvittana*); E8E10-dodecadienol which is the sex pheromone substance of the codling moth (*Cydia pomonella*); Z-11-tetradecenyl acetate which is the sex pheromone substance of the leaf roller (*Tortricidae*); Z3-Z13-octadecadienyl acetate and E3Z13-octadecadienyl acetate which are the sex pheromone substances of the peach tree borer (*Synanthedon exitiosa*); Z11-hexadecenal which is the sex pheromone substance of the American bollworm (*Helicoverpa armigera*); Z9-hexadecenal which is the pheromone substance of the oriental tobacco bud worm (*Heliothis assulta*); E8E10-dodecadienyl acetate which is the sex pheromone substance of the soybean pod borer (*Leguminivora glycinivorella*); Z-11-hexadecenyl acetate and Z-11-hexadecenal which are the sex pheromone substances of the diamondback moth (*Plutella xylostella*); Z-11-hexadecenyl acetate, Z-11-hexdecenol and n-hexadecyl acetate which are the sex pheromone substances of the cabbage armyworm (*Mamestra brassicae*); Z9E12-tetradecadienyl acetate and Z-9-tetradecenol which are the sex pheromone substances of the beat armyworm (*Spodoptera exigua*); Z9E11-tetradecadienyl acetate and Z9E12-tetradecadienyl acetate which are the sex pheromone substances of the common cutworm (*Spodoptera litura*); Z-9-tetradecenyl acetate which is the sex pheromone substance of the fall armyworm (*Spodoptera frugiperda*); E-4-tridecenyl acetate which is the sex pheromone substance of the tomato pinworm (*Keiferia lycopersicella*); Z-11-hexadecenal and Z-13-octadecenal which are the sex pheromone substances of the rice stem borer (*Scirpophaga incertulas*); 5,9-dimethylpentadecane and 5,9-dimethylhexadecane which are the sex pheromone substance of the coffee leaf miner (*Leucoptera coffeella*); 14-methyl-1-octadecene which is the sex pheromone substance of the peach leaf miner (*Lyonetia clerkella* L.); Z-13-icosen-10-one which is the sex pheromone substance of peach fruit moth (*Carposina sasakii*); 7,8-epoxy-2-methyloctadecane which is the sex pheromone substance of the gypsy moth (*Lymantria dispar dispar*); Z-13-hexadecen-1-nyl acetate which is the sex pheromone substance of the pine processionary moth (*Thaumetopoea pityocampa*); 2-butanol which is the sex pheromone substance of the white grub beetle (*Dasylepida ishigakiensis*); Z-7,15-hexadecadien-4-olide which is the sex pheromone substance of the yellowish elongate chafer (*Heptophylla picea*); n-dodecyl acetate which is the sex pheromone substance of the sugarcane wireworm (*Melanotus okinawensis*); E-9,11-dodecadienyl butyrate and E-9,11-dodecadienyl hexanate which are the sex pheromone substances of the sugarcane wireworm (*Melanotus sakishimensis*); (R)-Z-5-(oct-1-enyl)-oxacyclopentan-2-one which is the sex pheromone substance of the cupreous chafer (*Anomala cuprea*); hexyl hexanoate, E-2-hexenyl hexanoate and octyl butyrate which are the sex pheromone substances of the rice leaf bug (*Trigonotylus caelestialium*); hexyl butyrate, E-2-hexenyl butyrate and E-4-oxo-2-hexenal which are the sex pheromone substances of the sorghum plant bug (*Stenotus rubrovittatus*); (6R)-Z-3,9-dimethyl-6-isopropenyl-3,9-decadienyl propionate and (6R)-Z-3,9-dimethyl-6-isopropenyl-3,9-decadienol which are the sex pheromone substances of the white peach scale (*Pseudaulacaspis pentagona*); (S)-5-methyl-2-(1-propen-2-yl)-4-hexenyl 3-methyl-2-butenoate which is the sex pheromone substance of the vine mealybug (*Planococcus ficus*); Z-9-tricosene which is the sex pheromone substance of the housefly (*Musca domestica*); gentisyl quinone isovalerate which is the sex pheromone of the German cockroach (*Blattella germanica*); and 1,7-dioxaspiro[5.5]undecane which is the sex pheromone substance of the olive fruit fly (*Bactrocera oleae*).

Other examples of the pheromone substance to be used in the invention include a linear aliphatic aldehyde having from 12 to 20 carbon atoms, a linear aliphatic acetate having from 12 to 20 carbon atoms which is saturated or has one or more double bonds, a linear aliphatic alcohol having from 7 to 20 carbon atoms, a spiroacetal having from 7 to 15 carbon atoms, a linear aliphatic ketone having from 10 to 25 carbon atoms, an aliphatic hydrocarbon having from 10 to 30 carbon atoms and a carboxylic acid having from 10 to 20 carbon atoms, other than those exemplified above.

Specific examples of the linear aliphatic aldehyde having from 10 to 20 carbon atoms include Z-5-decenal, 10-undecenal, n-dodecanal, Z-9-dodecenal, E5Z10-dodecadienal, E8E10-dodecadienal, n-tetradecanal, Z7-tetradecenal, Z9-tetradecenal, Z11-tetradecenal, Z9E11-tetradecadienal, Z9Z11-tetradecadienal, Z9E12-tetradecadienal, Z9E11,13-tetradecatrienal, Z10-pentadecenal, E9Z11-pentadecadienal, n-hexadecanal, Z7-hexadecenal, E6Z11-hexadecadienal, E4Z6-hexadecadienal, E4E6Z11-hexadecatrienal, E10E12E14-hexadecatrienal, n-octadecanal, Z9-octadecenal, E14-octadecenal, E2Z13-octadecadienal, Z3Z13-octadecadienal, Z9Z12-octadecadienal, and Z9Z12Z15-octadecatrienal.

Specific examples of the linear aliphatic acetate having from 12 to 20 carbon atoms which is saturated or has a double bond include decyl acetate, Z3-decenyl acetate, Z4-decenyl acetate, undecyl acetate, Z7-undecenyl acetate, Z8-undecenyl acetate, E9-undecenyl acetate, dodecyl acetate, E7-dodecenyl acetate, Z7-dodecenyl acetate, E8-dodecenyl acetate, E9-dodecenyl acetate, 11-dodecenyl acetate, 10-methyldodecenyl acetate, tridecyl acetate, Z4-tridecenyl acetate, E6-tridecenyl acetate, E8-tridecenyl acetate, Z8-tridecenyl acetate, tetradecyl acetate, Z7-tetradecenyl acetate, E8-tetradecenyl acetate, Z8-tetradecenyl acetate, E9-tetradecenyl acetate, Z9-tetradecenyl acetate, E10-tetradecenyl acetate, Z10-tetradecenyl acetate, E12-tetradecenyl acetate, Z12-tetradecenyl acetate, 12-methyl-tetradecenyl acetate, pentadecyl acetate, Z8-pentadecenyl acetate, E9-pentadecenyl acetate, hexadecyl acetate, Z3-hexadecenyl acetate, Z5-hexadecenyl acetate, E6-hexadecenyl acetate, Z7-hexadecenyl acetate, Z9-hexadecenyl acetate, Z10-hexadecenyl acetate, Z12-hexadecenyl acetate, heptadecyl acetate, Z11-heptadecenyl acetate, octadecyl acetate, E2-octadecenyl acetate, Z11-octadecenyl acetate, and E13-octadecenyl acetate.

Specific examples of the linear aliphatic acetate having from 12 to 20 carbon atoms and having two or more double bonds include a conjugated diene-based and/or 1,4-pentadiene-based acetate such as Z3E5-decadienyl acetate, Z3E5-dodecadienyl acetate, E3Z5-dodecadienyl acetate, E4Z10-dodecadienyl acetate, Z5E7-dodecadienyl acetate, E5Z7-dodecadienyl acetate, Z8Z10-dodecadienyl acetate, 9,11-dodecadienyl acetate, E4Z7-tridecadienyl acetate, 11-methyl-Z9,12-tridecadienyl acetate, E3E5-tetradecadienyl acetate, E8E10-tetradecadienyl acetate, Z10Z12-tetradecadienyl acetate, Z10E12-tetradecadienyl acetate, E10Z12-tetradecadienyl acetate, E10E12-tetradecadienyl acetate, E11,13-tetradecadienyl acetate, Z8Z10-pentadecadienyl acetate, Z8E10-pentadecadienyl acetate, Z8Z10-hexadecadienyl acetate, Z10E12-hexadecadienyl acetate, Z11Z13-hexadecadienyl acetate, Z11E13-hexadecadienyl acetate, E11Z13-hexadecadienyl acetate, and Z11E14-hexadecadienyl acetate.

Specific examples of the linear aliphatic alcohol having from 7 to 20 carbon atoms include a saturated linear aliphatic alcohol and a linear aliphatic alcohol having one or more double bonds such as n-heptanol, Z4-heptenol, Z6-nonenol, Z6,8-nonadienol, E6,8-nonadienol, n-decanol, Z5-decenol, E5-decenol, n-undecanol, undecenol, 11-chloro-E8E10-undecadienol, n-dodecanol, Z5-dodecenol, Z7-dodecenol, E7-dodecenol, Z8-dodecenol, E8-dodecenol, Z9-dodecenol, E9-dodecenol, E10-dodecenol, 11-dodecenol, Z5E7-dodecadienol, E5Z7-dodecadienol, E5E7-dodecadienol, Z7Z9-dodecadienol, Z7E9-dodecadienol, E7Z9-dodecadienol, 8,9-difluoro-E8E10-dodecadienol, 10,11-difloro-E8E10-dodecadienol, 8,9,10,11-tetrafluoro-E8E10-dodecadienol, Z9,11-dodecadienol, E9,E11-dodecadienol, n-tridecanol, n-tetradecanol, Z5-tetradecenol, E5-tetradecenol, Z7-tetradecenol, Z8-tetradecenol, Z11-tetradecenol, E11-tetradecenol, Z9Z11-tetradecadienol, Z9E11-tetradecadienol, Z9Z12-tetradecadienol, Z9E12-tetradecadienol, Z10Z12-tetradecadienol, E10E12-tetradecadienol, n-pentadecanol, 6,10,14-trimethyl-2-pentadecanol, n-hexadecanol, Z9-hexadecenol, Z11-hexadecenol, E11-hexadecenol, Z7Z11-hexadecadienol, Z7E11-hexadecadienol, E10Z12-hexadecadienol, E10E12-hexadecadienol, Z11Z13-hexadecadienol, Z11E13-hexadecadienol, E11Z13-hexadecadienol, E11Z13-hexadecadienol, E4Z6Z10-hexadecatrienol, E4E6Z10-hexadecatrienol, n-octadecanol, Z13-octadecenol, E2Z13-octadecadienol, Z3Z13-octadecadienol, E3Z13-octadecadienol and n-eicosanol.

Specific examples of the spiroacetal having from 7 to 15 carbon atoms include 1,6-dioxaspiro[4.5]decane, 2-ethyl-1,6-dioxaspiro[4.4]nonane, 3-hydroxy-1,7-dioxaspiro[5.5]undecane, 4-hydroxy-1,7-dioxaspiro[5.5]undecane, 7-methyl-1,6-dioxaspiro[4.5] decane, 2-methyl-1,6-dioxaspiro[4.5] decane, 2,7-dimethyl-1,6-dioxaspiro[4.4]nonane, 2,4,8-trimethyl-1,7-dioxaspiro[5.5]undecane, 2-methyl-1,7-dioxaspiro[5.5]undecane, 1,7-dioxaspiro[5.6]dodecane, 2,8-dimethyl-1,7-dioxaspiro[5.5]undecane, 2,2,8-trimethyl-1,7-dioxaspiro[5.5]undecane, 2-ethyl-1,7-dioxaspiro[5.5]undecane, 2-methyl-1,7-dioxaspiro[5.6]dodecane, 2-ethyl-7-methyl-1,6-dioxaspiro[5.6]decane, 7-ethyl-2-methyl-1,6-dioxaspiro[5.6]decane, 2,7-diethyl-1,6-dioxaspiro[4.4]nonane, 2,7-dimethyl-1,6-dioxaspiro[4.6]undecane, 2-methyl-7-propyl-1,6-dioxaspiro[4.4]nonane, 3-hydroxy-2,8-dimethyl-1,7-dioxaspiro[5.5]undecane, 2-propyl-1,7-dioxaspiro[5.5]undecane, 2-ethyl-8-methyl-1,7-dioxaspiro[5.5]undecane, 8-ethyl-2-methyl-1,7-dioxaspiro[5.5]undecane, 2,7-diethyl-1,6-dioxaspiro[4.5]decane, 2,7-dipropyl-1,6-dioxaspiro[4.4]nonane, 7-butyl-2-methyl-1,6-dioxaspiro[4.5]decane, 8-methyl-2-propyl-1,7-dioxaspiro[5.5]undecane, and 2-propyl-8-methyl-1,7-dioxaspiro[5.5]undecane.

Specific examples of the linear aliphatic ketone having from 10 to 25 carbon atoms include heptadecan-2-one, Z12-nonadecen-9-one, Z6Z9-nonadecadien-3-one, Z13-icosen-10-one, Z6-heneicosen-11-one, Z6-heneicosen-9-one, Z6E8-heneicosadien-11-one, Z6E9-heneicosadien-11-one, Z6Z9-heneicosadien-11-one, and Z7-tricosen-11-one.

Specific examples of the aliphatic hydrocarbon having from 10 to 30 carbon atoms include 1E11-pentadecadiene, 1Z11-pentadecadiene, 5,9-dimethylpentadecane, 2-methylhexadecane, 3,13-dimethylhexadecane, 5,9-dimethylhexadecane, n-heptadecane, 2-methylheptadecane, 2,5-dimethylheptadecane, 5-methylheptadecane, 5,11-dimethylheptadecane, 7-methylheptadecane, 7,11-dimethylheptadecane, Z3Z6Z9-heptadecatriene, Z6Z9-heptadecadiene, Z7-octadecene, 10,14-dimethyl-1-octadecene, 5,9-dimethyloctadecane, 2-methyloctadecane, 14-methyloctadecane, Z3Z6Z9-octadecatriene, n-nonadecane, 2-methylnonadecane, 9-methylnonadecane, Z3Z6Z9Z11-nonadecatetraene, 1E3Z6Z9-nonadecatetraene, Z3Z6Z9-nonadecatriene, Z6Z9-nonadecadiene, Z9-nonadecene, n-eicosane, Z9-eicosene, Z3Z6-eicosadiene, Z3Z6Z9-eicosatriene, 1Z3Z6Z9-eicosatetraene, 1Z3Z6Z9-heneicosatetraene, n-heneicosane, Z3Z6-heneicosadiene, Z6Z9-heneicosadiene, Z6Z9-heneicosatriene, Z3Z6Z9-heneicosatriene, Z6Z9,20-heneicosatriene, Z3Z6Z9-heneicosatriene, Z6-13-methylheneicosatriene, Z9-heneicosene, n-docosaene, Z3Z6Z9-docosatriene, Z6Z9-docosadiene, n-tricosane, Z7-tricosene, Z3Z6Z9-tricosatriene, Z6Z9-tricosadiene, n-tetracosane, n-pentacosane, Z3Z6Z9-pentacosatriene, n-hexacosane, n-heptacosane, n-octacosane, and n-nonacosane.

Specific examples of the carboxylic acid having from 10 to 20 carbon atoms are not particularly limited insofar they contain a carboxyl group. Examples include carboxylic acids having, in the carbon skeleton thereof, two or more methyl groups, one or more double bond or the like, such as 3,5-dimethyldodecanoeic acid, Z-5-undecenoic acid, E-5-undecenoic acid, and (E,Z)-3,5-tetradecadienoic acid.

Specific examples of the attractant include an aliphatic carboxylic acid such as formic acid, acetic acid, propionic acid, n-butyric acid, isobutyric acid, n-valeric acid, isovaleric acid, caproic acid, isocaproic acid, E2-butenoic acid, 2-hydroxypropionic acid and malonic acid; an aliphatic aldehyde such as acetaldehyde, propanal, pentanal and E2-hexanal; an aliphatic ketone such as 2-butanone, pentane-2,4-dione and cyclohexanone; an aliphatic carboxylate ester such as ethyl lactate, ethyl acetate, isoamyl acetate, Z3-hexenyl acetate, decyl acetate, hexyl 2-methylbutyrate, butyl hexanoate, ethyl octanoate, ethyl nonanoate, ethyl decanoate, ethyl undecanoate, ethyl dodecanoate, ethyl myristate, ethyl palmitate, ethyl E2Z4-decadienoate, tert-butyl 2-methyl-4-cyclohexenecarboxylate and tert-butyl 4 (or 5)-chloro-2-methyl-cyclohexanecarboxylate; an aliphatic alcohol such as ethanol, isobutyl alcohol, isopentyl alcohol, 2-ethylhexanol, Z3-hexenol, 1-octen-3-ol, nonanol, decanol, cyclohexanol, acetoin and propane 1,2-diol; an aliphatic ether such as diethyl ether and acetal; an aliphatic hydrocarbon such as α,β-ionone, undecane, tridecane, hexadecane, heptadecane and Z9-tricosene; an aromatic compound such as methyl phenylacetate, ethyl phenylacetate, propyl phenylacetate, phenetyl phenylacetate, Z3-hexenyl benzoate, eugenol, methyl isoeugenol, methyl eugenol, veratric acid, 2-allyloxy-3-ethoxybenzaldehyde, 4-(p-acetoxyphenyl)-2-butanone, 4-(p-hydroxyphenyl)-2-butanone (Raspberry ketone), anisylacetone, methyl anthranilate, ethyl anthranilate, benzyl salicylate, methyl salicylate, phenethyl alcohol, phenethyl propionate, phenethyl butyrate, anethole, vanillin, ethyl vanillin, isovanillin, heliotropin, piperonal acetone and phthiocol; a heterocyclic compound such as maltol, ethyl maltol, 2,5-dimethylpyrazine, γ-(4-pentenyl)-γ-butyrolactone, δ-nonyllactone and frontalis; a sulfur-containing compound such as dimethyl disulfide, dimethyl trisulfide, dipropyl disulfide, methyl isothiocyanate and 3-butenyl isothiocyanate; a nitrogen-containing compound such as trimethylamine, hexylamine, 1,4-diaminobutane, allylnitrile and methyl 2-amino-3-methylvalerate; and a terpene compound such as geraniol, farnesol, linalool, linalool oxide, citronellol, cineol, geranyl acetate, citronellyl acetate, citral, carvone, d-limonene, β-pinene, farnesene and 4,8-dimethyl-1,E3,7-nonatriene.

Other specific examples of the attractant include an essential oil such as angelica oil, citronella oil and mustard oil; and an extract from a plant such as aloe and eucalyptus.

Specific examples of the repellent include an aliphatic carboxylic acid such as Z9Z12-octadienoic acid and 3,7,11-trimethyl-6,10-dodecadinoic acid; an aliphatic aldehyde such as E2-hexenal, Z2E6-3,7-dimethyloctadienal, 3,7-dimethyl-6-octenal and E2Z6-nonadienal; an aliphatic ketone such as 2-heptanone, 2-dodecanone, 2-tridecanone, 3-methyl-2-cyclohexenone, E3E5-octadien-2-one and E3Z7-decadien-2-one; an aliphatic carboxylate ester such as butyl acetate, octyl acetate, methyl myristate, methyl palmitate and methyl 6-n-pentylcyclonexene-1-carboxylate; an aliphatic alcohol such as octanol, 1-octen-3-ol, 2-ethyl-1,3-hexanediol, menthol and n-hexyltriethylene glycol monoether; an aliphatic hydrocarbon such as tridecane; an aromatic compound such as cinnamic alcohol, cinnamic aldehyde, methyleugenol, phenyl acetaldehyde, benzaldehyde, anethole, diethyltoluamide, N,N-diethyl-3-methylbenzamide (DEET), dimethyl phthalate, dioctyl phthalate and naphthalene; a heterocyclic compound such as γ-nonyllactone, butyl 3,4-dihydro-2,2-dimethyl-4-oxo-2H-pyran-6-carboxylate, furfural and 4-octanoyl morpholine; a sulfur-containing compound such as propyl isothiocyanate; a nitrogen-containing compound such as methyl piperidine, 2,6-dimethylpiperidine and 2-ethylpiperidine; and a terpene compound such as geraniol, cineol, linalool, terpineol, citral, citronellal, neryl formate, α-pinene, carvone, d-limonene and camphor.

Additional examples may include an essential oil such as rose geranium oil, sandalwood oil, pepper oil (peppermint oil) and lemongrass oil; and an extract from a plant such as cinnamon, camphor, clover, thyme, geranium, bergamot, laurel, pine, *Gaultheria adenothrix*, pennyroyal, eucalyptus and neem tree.

Further examples may include a pyrethroid compound such as pyrethrin, allethrin, phthalthrin, resmethrin, furamethrin, phenothrin, permethrin, cyphenothrin, purallethrin, etofenprox, empenthrin and transfluthrin.

The oil gelling agent to be used in the invention has, in the molecule thereof, at least one polar functional group capable of forming an intermolecular hydrogen bond such as a carboxyl group, a hydroxyl group, an ester group or an amide group, so that the intermolecular hydrogen bonds are present through the polar functional group. When the oil gelling agent is dissolved uniformly in the volatile substance by heating (preferably at from 60 to 150° C.), the intermolecular hydrogen bonds of the oil gelling agent are cut temporarily, but are formed again by cooling (including cooling by being left standing). Since a large amount of the volatile substance exists around the molecules of the oil gelling agent, the oil gelling agent forms the intermolecular hydrogen bonds again while incorporating therein the volatile substance. Only weak interaction such as Van der Waals force works between the volatile substance and the molecules of the oil gelling agent so that the volatility of the volatile substance even after gelling is almost the same as that before gelling.

Specific examples of the oil gelling agent include an amino acid derivative, a long-chain fatty acid, a polyvalent metal salt of a long-chain fatty acid, a sugar derivative and wax. Of these examples, an amino acid derivative and a long-chain fatty acid are particularly preferred.

Specifically preferred examples of the amino acid derivative include an amino-acylated and carboxyl-esterified or carboxyl-amidated derivative of an amino acid having from 2 to 15 carbon atoms, such as di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, N-lauroyl-L-glutamic acid dibutylamide, and N-ethylhexanoyl-L-glutamic acid dibutylamide. Of these examples, N-lauroyl-L-glutamic acid dibutylamide and N-ethylhexanoyl-L-glutamic acid dibutylamide are particularly preferred.

Specific examples of the long-chain fatty acid include a saturated or unsaturated fatty acid having from 8 to 24 carbon atoms, and an analog of a long-chain fatty acid such as 12-hydroxystearic acid. Specific examples of the saturated fatty acid include octanoic acid, 2-ethylhexanoic acid, decanoic acid, lauric acid, myristic acid, stearic acid, palmitic acid, arachidic acid and behenic acid. Specific examples of the unsaturated fatty acid include palmitoleic acid, oleic acid, vaccenic acid, linoleic acid, linolenic acid, arachidonic acid, icosadienoic acid and erucic acid.

Specific examples of the metal salt of a long-chain fatty acid include a metal salt of the long-chain fatty acid described above and a metal salt of a saturated fatty acid, for example, having a carbon chain of 18 carbon atoms such as aluminum stearate, magnesium stearate, manganese stearate, iron stearate, cobalt stearate, calcium stearate and lead stearate.

Specific examples of the saccharide derivative include a dextrin fatty acid ester such as dextrin laurate, dextrin myristate, dextrin palmitate, dextrin margarate, dextrin stearate, dextrin arachidate, dextrin lignocerate, dextrin cerotate, dextrin 2-ethylhexanoate palmitate and dextrin palmitate stearate; a sucrose fatty acid ester such as sucrose palmitate, sucrose stearate and sucrose acetate/stearate; a fructooligosaccharide fatty acid ester such as fructooligosaccharide stearate and fructooligosaccharide 2-etylhexanoate; and a benzylidene derivative of sorbitol such as monobenzylidene sorbitol and dibenzylidene sorbitol.

Specific examples of the wax include haze wax (Japan wax derived from *Rhus succedanea* seeds; main component: triglyceride of palmitic acid), urushi wax (Japan wax derived from *Rhus verniciflua*; main component: glyceride palmitate), carnauba wax (myricyl cerotate and myricyl alcohol), sugarcane wax (myricyl palmitate), palm wax (myricyl palmitate), beeswax (cerotic acid and myricyl palmitate), whale wax (cetyl palmitate), wool wax (ceryl alcohol and/or myristic acid) and paraffin wax (linear hydrocarbon).

A critical gelling concentration at which a volatile substance gels differs, depending on the structure of a polar functional group, the strength of hydrogen bonds and an asymmetric structure of the oil gelling agent. The strength of hydrogen bonds of the oil gelling agent is sometimes weakened by the coordination of the functional group (polar group) and a non-polar group of the volatile substance. The critical gelling concentration differs, depending on the chemical structure of the volatile substance and the kind of the gelling agent. In consideration of the release performance and cost, the gel composition is charged in the vessel desirably at a concentration near the critical gelling concentration. More specifically, the insect pest-targeting gel composition comprises therein from 70.0 to 99.0% by weight, preferably from 85.0 to 99.0% by weight, still more preferably from 90.0 to 99.0% by weight of the volatile substance. When the amount of the volatile substance in the insect pest-targeting gel composition is less than 70.0% by weight, the active ingredient of the volatile substance is enclosed in the gel so that the volatile substance cannot be released stably, thereby making it impossible to achieve long-term and constant sustained-release. In addition, it may increase the cost. When the volatile substance in the insect pest-targeting gel composition exceeds 99.0% by weight, the insect pest-targeting gel composition having fluidity only can be obtained.

The content (% by weight) of the one or more volatile substances in the insect pest-targeting gel composition differs, depending on the kind of the one or more volatile substances or the oil gelling agent. For example, among olive insect pests in the Mediterranean and African areas, the olive fruit fly (*Bactrocera oleae*) which has recently been detected also in North America has caused serious damage to olive production because its larvae hatched from eggs laid on olive fruit by females eat the fruit. As the damage caused by this insect pest, not only a reduction in the yield of olive but also deterioration in the flavor of olive due to an increased acidity is known. When 1,7-dioxaspiro[5.5]undecane, a pheromone substance of olive fruit fly (*Bactrocera oleae*), is gelled with an amino acid derivative such as N-lauroylglutamic acid dibutylamide, the content of 1,7-dioxaspiro[5.5]undecane is more preferably from 95.0 to 99.0% by weight. When 1,7-dioxaspiro[5.5]undecane is gelled with a long-chain fatty acid such as stearic acid, the content of 1,7-dioxaspiro[5.5]undecane is more preferably from 75.0 to 85.0% by weight.

In the conventional gel composition, it is the common practice to dilute the gel composition with a solvent or the like to form a fluid gel in order to avoid a problem that the surface of the insect pest-targeting gel composition is dried to enclose the active ingredient of the volatile substance in the gel. However, when the gel contains a solvent or the like, it is difficult to obtain a stable release rate because due to the volatility of the solvent, the concentration of the volatile substance in the gel composition changes along with the sustained release. Moreover, this dilution causes problems such as necessity of measures against liquid leakage and unnecessary increase in volume. With the foregoing in view, as described above, according to the invention, provided is an insect pest-targeting gel composition comprising a volatile substance and an oil gelling agent, wherein the volatile substance is comprised in an amount of from 70.0 to 99.0% by weight by the insect pest-targeting gel composition.

The insect pest-targeting gel composition of the invention does not require measures against liquid leakage because it is a non-fluid gel comprising, in addition to the volatile substance, substantially only the oil gelling agent and an optional additive which will be described later. Furthermore, it does not cause the unnecessary volume increase because it does not comprise a solvent or the like. Moreover, the volatile substance in the insect pest-targeting gel composition is released to the outside space and the gelling agent which has contributed to the gelling of the sustainably released volatile substance remains on the gel surface in powder form so that the concentration of the volatile substance in the insect pest-targeting gel composition becomes substantially constant throughout the release period, making it possible to achieve a stable release rate.

Thus, the insect pest-targeting gel composition of the invention is in non-fluid form, can be stored for a long period of time, and fluidization of the insect pest-targeting gel composition does not occur insofar as it is stored at normal temperature.

The insect pest-targeting gel composition may comprise an additive. The examples of the additive include an antioxidant such as a synthetic antioxidant, e.g., BHT (butylhydroxytoluene), BHA (butylhydroxyanisole), ethyl protocatechuate, isoamyl gallate and propyl gallate, and a natural antioxidant, e.g., NDGA (nordihydroguaiaretic acid) and guaiac gum; and a ultraviolet absorber such as a para-aminobenzoic acid-based one, e.g., octyl para-dimethylaminobenzoate, a benzophenone derivative such as oxybenzone (2-hydroxy-4-methoxy-benzophenone) and 2-hydroxy-4-octoxybenzophenone, a methoxycinnamic acid derivative and a salicylic acid derivative. The content of each additive in the insect pest-targeting gel composition is preferably from 0.01 to 5% by weight and the total content of them is preferably from 0.02 to 10% by weight.

The insect pest-targeting gel composition can be obtained by heating the volatile substance, the oil gelling agent and an optional additive preferably at about 60 to 150° C. for dissolution, and then cooling the resulting solution. The cooling is preferably cooling by being left standing.

In the invention, the sustained release preparation can be obtained by introducing an insect pest-targeting gel composition into a vessel having an opening portion for releasing one or more volatile substances therefrom and made of a material not permitting penetration of the one or more volatile substances therethrough. The one or more volatile substances evaporate from the surface of the insect pest-targeting gel composition thus introduced in the vessel, and are released to an outside space from the opening portion through unoccupied space in the vessel present between the surface of the insect pest-targeting gel composition and the opening portion.

Figure 1:
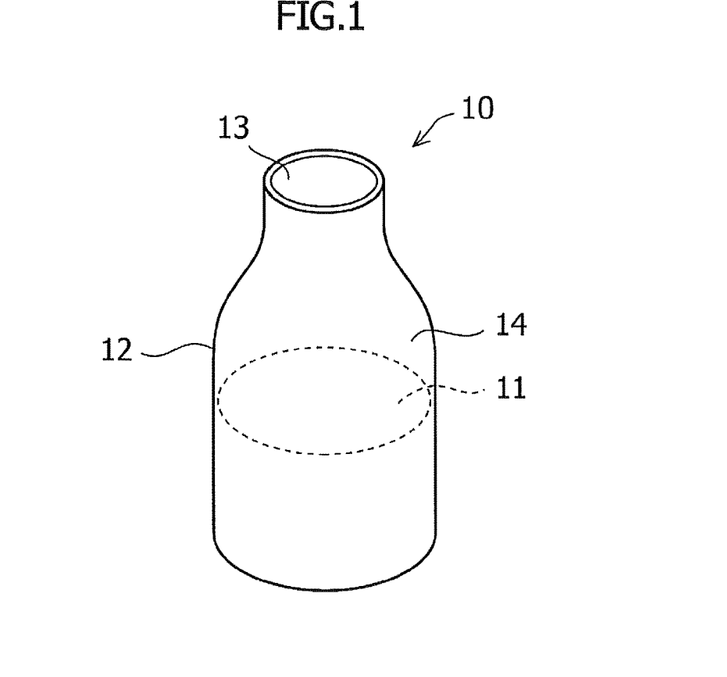
FIG. 1 shows one example of a sustained release preparation.

An example of the sustained release preparation is shown in FIG. 1. A sustained release preparation 10 comprises an insect pest-targeting gel composition 11 in a vessel 12 having an opening portion 13. From the surface of the insect pest-targeting gel composition 11, one or more volatile substances evaporate. The one or more volatile substances are released to the outside space from the opening portion 13 through unoccupied space 14 in the vessel. Although FIG. 1 shows a bottle-shaped vessel, the shape of the vessel is not particularly limited insofar as it permits introduction of the insect pest-targeting gel composition.

The release rate of one or volatile substances can be regulated by changing the surface area of the insect pest-targeting gel composition, the area of the opening portion, the volume or shape of the unoccupied space in the vessel, or the like.

The greater the surface area of the insect pest-targeting gel composition, the higher the evaporation rate of the one or more volatile substances to the unoccupied space in the vessel. The greater the area of the opening portion, the higher the release rate of the one or more volatile substances from the opening portion to the outer space.

The volume or shape of the unoccupied space in the vessel plays a role of balancing between the evaporation rate of the one or more volatile substances from the surface of the insect pest-targeting gel composition to the unoccupied space in the vessel and the release rate of the one or more volatile substances from the opening portion to the outer space. For example, when the evaporation rate of the one or more volatile substances from the surface of the insect pest-targeting gel composition are higher than the release rate from the opening portion, the volatile substances continue to evaporate to the unoccupied space in the vessel until the partial pressure reaches a saturated vapor pressure. The concentration nN of the one or more volatile substances in the unoccupied space in the vessel upon evaporation is represented by the following equation (1):

$$n/V = p/RT \tag{1}$$

wherein, n represents the mole number (mol) of the one or more volatile substances in vapor form in the unoccupied space, V represents the volume (l) of the unoccupied space, p represents the partial pressure (atm) of the vapor of the one or more volatile substances, R represents a gas constant $(1 \cdot atm \cdot K^{-1} \cdot mol^{-1})$, and T represents an absolute temperature (K).

The concentration n/V becomes constant when the temperature is constant so that a stable release rate can be achieved. However, an extremely large volume of the unoccupied space in the vessel retards the initial release rate because it takes a long time to reach a saturated vapor pressure. In addition, the period during which a release rate decreases with the elapsed time is prolonged because all of the one or more volatile substances are present in gas form in the latter half of the release period. On the other hand, when the volume of the unoccupied space in the vessel is extremely small and the surface of the insect pest-targeting gel composition is located very close to the opening portion, it is sometimes difficult to suppress a release rate. Accordingly, the unoccupied space in the vessel is preferably the volume which is suited for the volatility of the one or more volatile substances and a desired release rate.

The release rate of one or more volatile substances can also be regulated by the shape of the unoccupied space in the vessel. For example, supposing that there are two sustained release preparations equal in the volume of the unoccupied space in the vessel and also equal in the fundamental shape, but one of them has a vessel having a capillary-like unoccupied space narrowing toward the opening portion and the other has a vessel having an unoccupied space not narrowing toward the opening portion, the release rate of the vessel having a capillary-like unoccupied space decreases with high possibility.

The shape of the vessel to be used for the sustained release preparation is not particularly limited insofar as it permits introduction of the insect pest-targeting gel composition therein. The volume of the vessel is preferably from 1.0 to 100 times, more preferably from 1.1 to 50 times the volume of the insect pest-targeting gel composition. When the area of the opening portion of the vessel falls within a range of preferably from 0.001 to 100 times, more preferably from 0.01 to 10 times the surface area of the insect pest-targeting gel composition, a stable release rate can be kept. The amount of one or more volatile substances and the surface area of the insect pest-targeting gel composition can be regulated desirably in order to achieve a release rate and a release period suited for the intended use of the sustained release preparation.

According to the invention, the sustained release preparation is made of a material not permitting the penetration of one or more volatile substances. Examples of the material of the vessel include thermoplastic polymers, for example, polyesters such as polyethylene terephthalate, polyamides such as 6,6-nylon, and fluorinated resins such as Teflon (registered trade mark); glass; paper; minerals such as zeolite; and metals.

According to the invention, the opening portion of the sustained release preparation may be covered with a film through which one or more volatile substances can penetrate. Even the release rate can be regulated by the material or thickness of the film. The film can also prevent invasion of foreign substances in the vessel. Moreover, use of a light blocking film can prevent decomposition of a volatile substance that is unstable to light.

Figure 2:
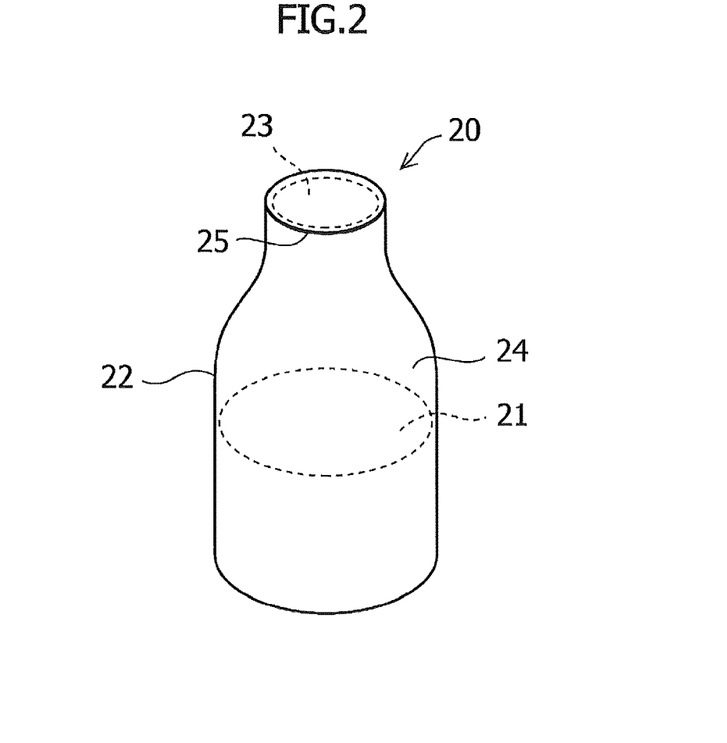
FIG. 2 shows one example of a sustained release preparation comprising a vessel having an open portion covered with a film which transmits one or more volatile substances.

An example of the sustained release preparation having the opening portion covered with a film capable of transmitting one or more volatile substances therethrough is shown in FIG. 2. A sustained release preparation 20 comprises a vessel 22 having an opening portion 23, and an insect pest-targeting gel composition 21 in the vessel. One or more volatile substances evaporate from the surface of the insect pest-targeting gel composition 21, and are released to the outside space from a film 25 covering the opening portion 23 therewith through an unoccupied space 24 in the vessel.

Specific examples of the film material include thermoplastic polymers such as high-density polyethylene, polypropylene, ethylene-propylene copolymers, ethylene-vinyl acetate copolymers, ethylene-acrylate ester-based copolymers, polyvinyl acetate, polyvinyl chloride-based resins, polymethyl methacrylate, polyvinyl alcohol, polyvinylidene chloride, polybutylene, methyl methacrylate-styrene copolymers, methylpentene resins, ionomers, polyacetal, cellulose acetate, cellulose acetate butylate, polyvinylidene fluoride and silicon resins. Additional examples include condensation polymers between at least one dicarboxylic acid and at least one polyol, wherein the at least one dicarboxylic acid is selected from oxalic acid, malonic acid, succinic acid, glutaric acid, adipic acid, sebacic acid, fumaric acid and maleic acid, and the at least one polyol is selected from ethylene glycol, propylene glycol, butanediol, pentanediol, hexanediol, octanediol and decanediol; condensation polymers of at least one monomer selected from lactic acid, hydroxyvaleric acid, hydroxycaproic acid and hydroxycapric acid; and aliphatic polyester-based thermoplastic polymers such as polycaprolactone. To these polymer materials, a lubricant, a plasticizer, a stabilizer, a pigment or a filler may be added to improve their processability.

Thickness of the film is preferably from 10 to 400 μm, more preferably from 20 to 250 μm. The film having a thickness less than 10 μm may be broken during sustained release because of insufficient strength, while the film having a thickness exceeding 400 μm may be required to have a large area because of slow transmission of one or more volatile substances.

EXAMPLES

The invention will be explained based on Examples. However, it should not be construed that the invention is limited to Examples.

Example 1

After 110.5 mg of 1,7-dioxaspiro[5.5]undecane and 3.4 mg of N-lauroylglutamic acid dibutylamide were added to a cylindrical glass vessel having an inner diameter of 4 mm and an internal volume of 0.5 ml and having an opening portion with a diameter of 4 mm at the upper part of the vessel, the vessel was sealed with a lid and heated at 80° C. for 2 minutes to form a uniform solution. The solution was then gradually allowed to cool to room temperature. As a result, an insect pest-targeting gel composition in non-fluid form was obtained.

Then, the lid of the cylindrical vessel was removed, and a weight change of the volatile substance contained in the gel composition at 30° C. was measured so that the release rate was determined. The results are shown in FIG. 3.

Figure 3:
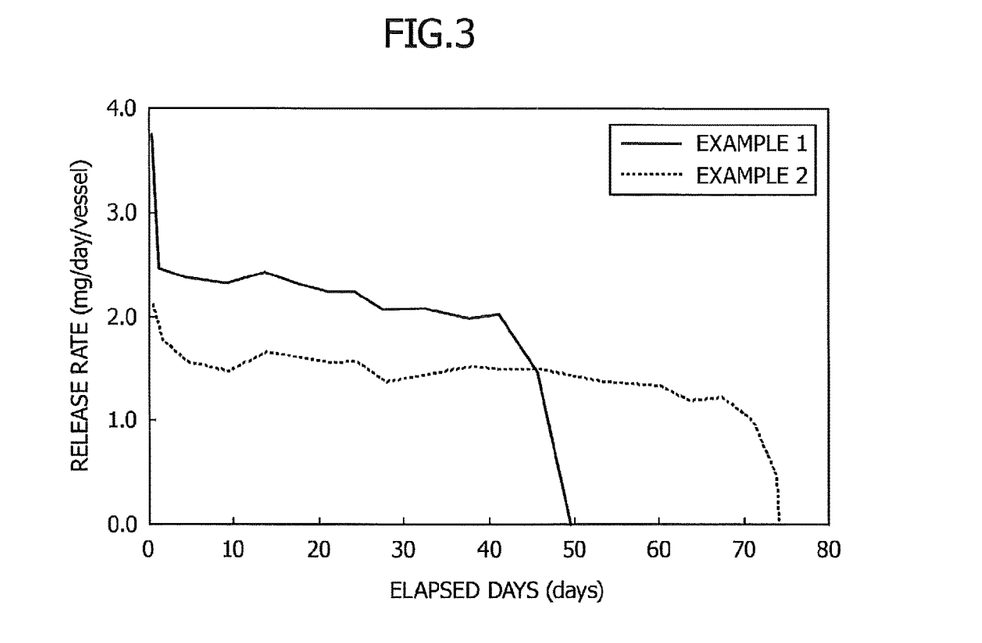
FIG. 3 is a graph showing the relationship between elapsed days and a release rate in Examples 1 and 2.

As shown in FIG. 3, the resulting sustained release preparation showed a stable release rate for 40 days.

Example 2

A sustained release preparation was produced and the release rate at 30° C. was determined in the same manner as in Example 1 except that the opening portion of the vessel was covered with a 40 μm-thick polyethylene film. The results are shown in FIG. 3.

As shown in FIG. 3, by covering the opening portion with the film, the release rate was suppressed and the release period was prolonged in comparison with Example 1.

Example 3

A sustained release preparation was produced and the release rate at 30° C. was determined in the same manner as in Example 1 except that a cylindrical glass vessel having an inner diameter of 10 mm and an internal volume of 2 ml was used and an opening portion with a diameter of 4 mm at the upper part of the vessel was covered with a 40 μm-thick polyethylene film. The results are shown in FIG. 4.

Figure 4:
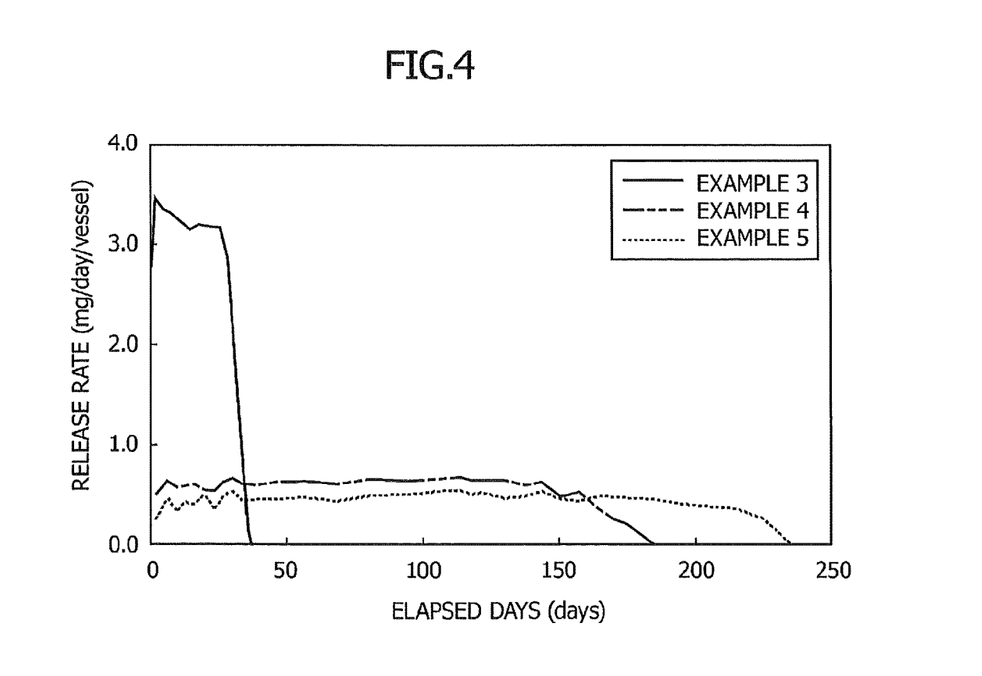
FIG. 4 is a graph showing the relationship between elapsed days and a release rate in Examples 3 to 5.

As shown in FIG. 4, in proportion to an increase in the surface area of the gel composition in comparison with that of Example 2, the sustained release preparation had an increased release rate and a decreased release period.

Example 4

A sustained release preparation was produced and the release rate was determined in the same manner as in Example 3 except that the opening portion was covered with a 100-μm thick polyethylene film. The results are shown in FIG. 4.

As shown in FIG. 4, since the opening portion was covered with a polyethylene film thicker than that of Example 3, the release rate was suppressed and the release period was prolonged.

Example 5

A sustained release preparation was produced and the release rate was determined in the same manner as in Example 3 except that the opening portion was covered with a 200-μm thick polyethylene film. The results are shown in FIG. 4.

As shown in FIG. 4, since the opening portion was covered with a film thicker than that of Example 3 or 4, the release rate was suppressed and the release period was prolonged.

Example 6

A sustained release preparation was produced and the release rate was determined in the same manner as in Example 3 except for use of 110.5 mg of 1,7-dioxaspiro [5.5]undecane and 27.0 mg of dextrin palmitate ("Rheopearl TL", product of Chiba Flour Milling). The results are shown in FIG. 5.

Figure 5:
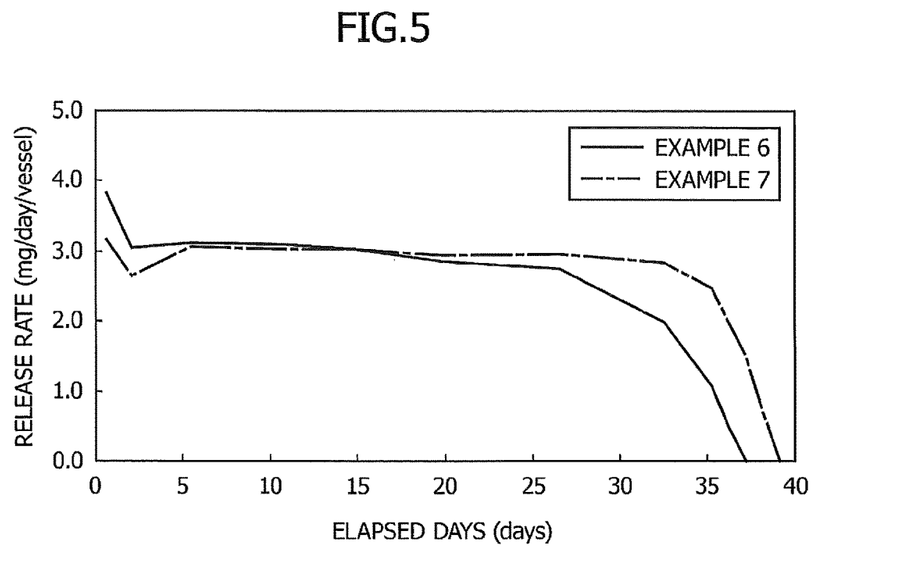
FIG. 5 is a graph showing the relationship between elapsed days and a release rate in Examples 6 and 7.

As shown in FIG. 5, the sustained release preparation maintained a stable release rate for at least one month in the same manner as in Example 3.

Example 7

A sustained release preparation was produced and the release rate was determined in the same manner as in Example 3 except for use of 110.5 mg of 1,7-dioxaspiro [5.5]undecane and 27.5 mg of stearic acid. The results are shown in FIG. 5.

As shown in FIG. 5, the sustained release preparation maintained a stable release rate for at least one month in the same manner as in Example 3 (same as above).

Example 8

After 10.13 g of d-limonene and 0.43 g of N-lauroylglutamic acid dibutylamide were added to a cylindrical glass vessel having an inner diameter of 31 mm and an internal volume of 50 ml and having an opening portion with a diameter of 22 mm at the upper part of the vessel, the vessel was sealed with a lid and heated at 80° C. for 2 minutes to from a uniform solution. The solution was then gradually allowed to cool to room temperature. As a result, an insect pest-targeting gel composition in non-fluid form was obtained.

Then, the lid of the cylindrical vessel was removed, and a weight change of the volatile substance contained in the gel composition at 30° C. was measured so that the release rate was determined. The results are shown in FIG. 6.

Figure 6:
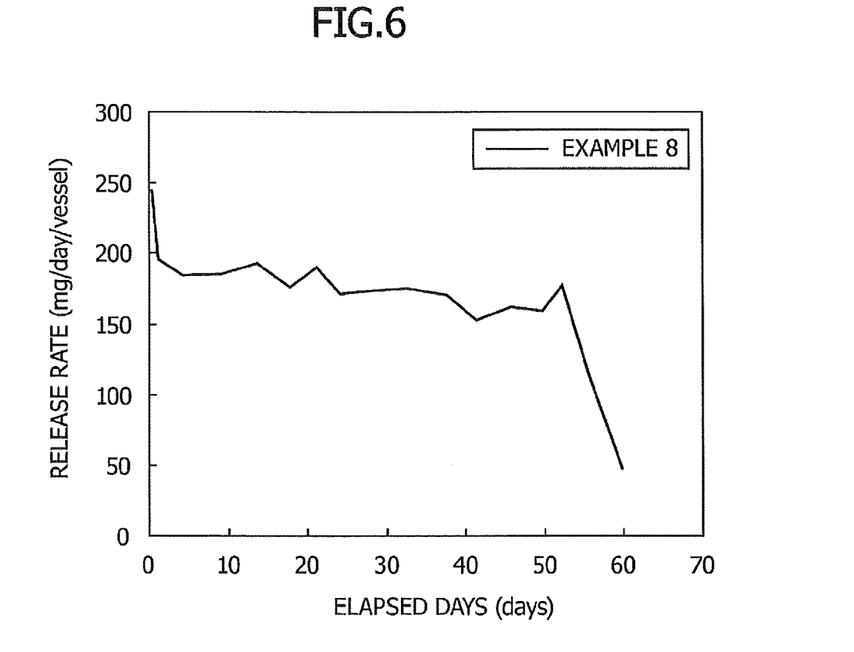
FIG. 6 is a graph showing the relationship between elapsed days and a release rate in Example 8.

As shown in FIG. 6, the sustained release composition showed a stable release rate for 50 days.

Example 9

A sustained release preparation was produced and the release rate at 30° C. was determined in the same manner as in Example 8 except that 134.2 g of methyleugenol was used instead of d-limonene and the amount of N-lauroylglutamic acid dibutylamide was changed to 4.0 mg. The results are shown in FIG. 7.

Figure 7:
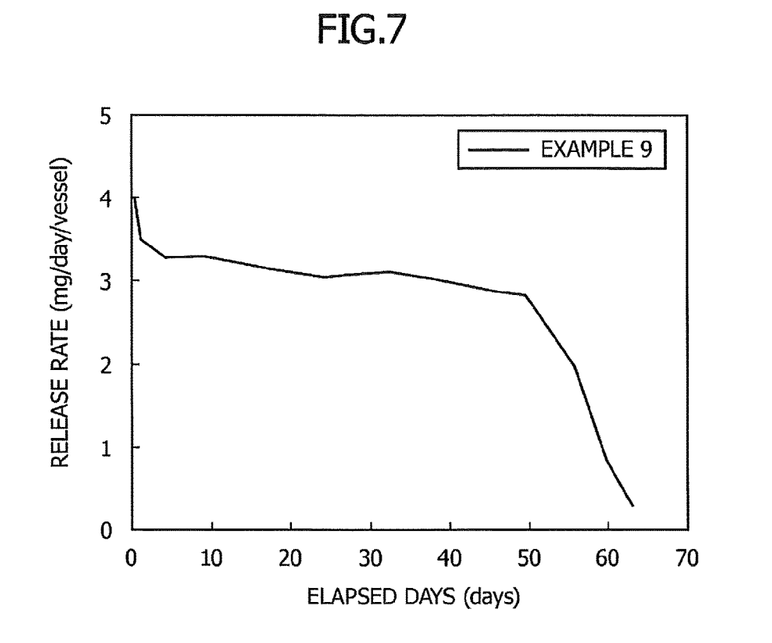
FIG. 7 is a graph showing the relationship between elapsed days and a release rate in Example 9.

As shown in FIG. 7, the preparation thus obtained showed a stable release rate for 50 days.

Example 10

A sustained release preparation was produced and the release rate at 40° C. was determined in the same manner as in Example 8 except that 102.2 mg of Z-8-dodecenyl acetate was used instead of d-limonene and the amount of N-lauroylglutamic acid dibutylamide was changed to 3.1 mg. The results are shown in FIG. 8.

Figure 8:
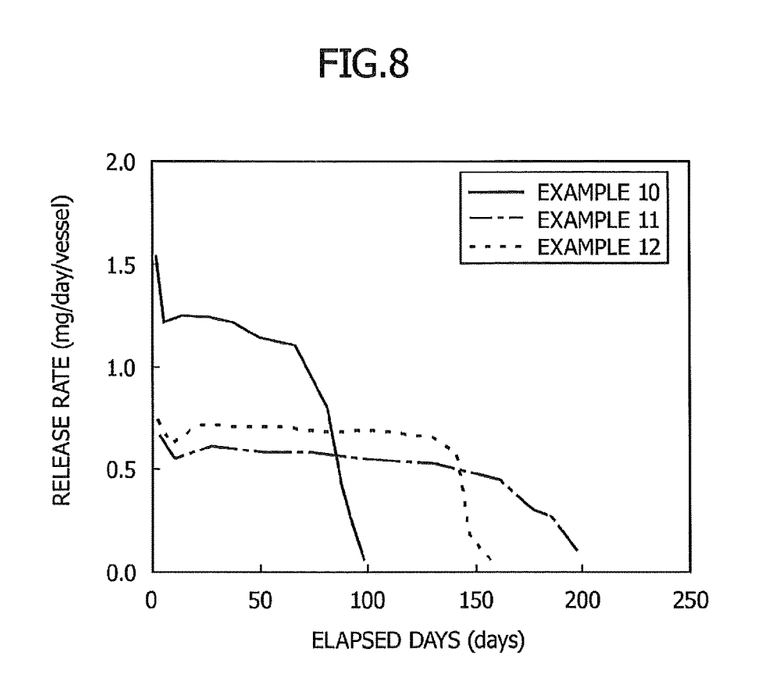
FIG. 8 is a graph showing the relationship between elapsed days and a release rate in Examples 10 to 12.

As shown in FIG. 8, the preparation thus obtained showed a stable release rate for 80 days.

Example 11

A sustained release preparation was produced and the release rate at 40° C. was determined in the same manner as in Example 8 except that 102.6 mg of E,Z-7,9-dodecadienyl acetate was used instead of d-limonene and the amount of N-lauroylglutamic acid dibutylamide was changed to 3.1 mg. The results are shown in FIG. 8.

As shown in FIG. 8, the preparation thus obtained showed a stable release rate for 160 days.

Example 12

A sustained release preparation was produced and the release rate at 40° C. was determined in the same manner as in Example 8 except that 100.3 mg of E,E-8,10-dodecadienol was used instead of d-limonene and the amount of N-lauroylglutamic acid dibutylamide was changed to 9.3 mg. The results are shown in FIG. 8.

As shown in FIG. 8, the preparation thus obtained showed a stable release rate for 140 days.

Example 13

A sustained release preparation was produced and the release rate at 50° C. was determined in the same manner as in Example 8 except that 102.2 mg of Z-13-icosen-10-one was used instead of d-limonene and the amount of N-lauroylglutamic acid dibutylamide was changed to 3.1 mg. The results are shown in FIG. 9.

Figure 9:
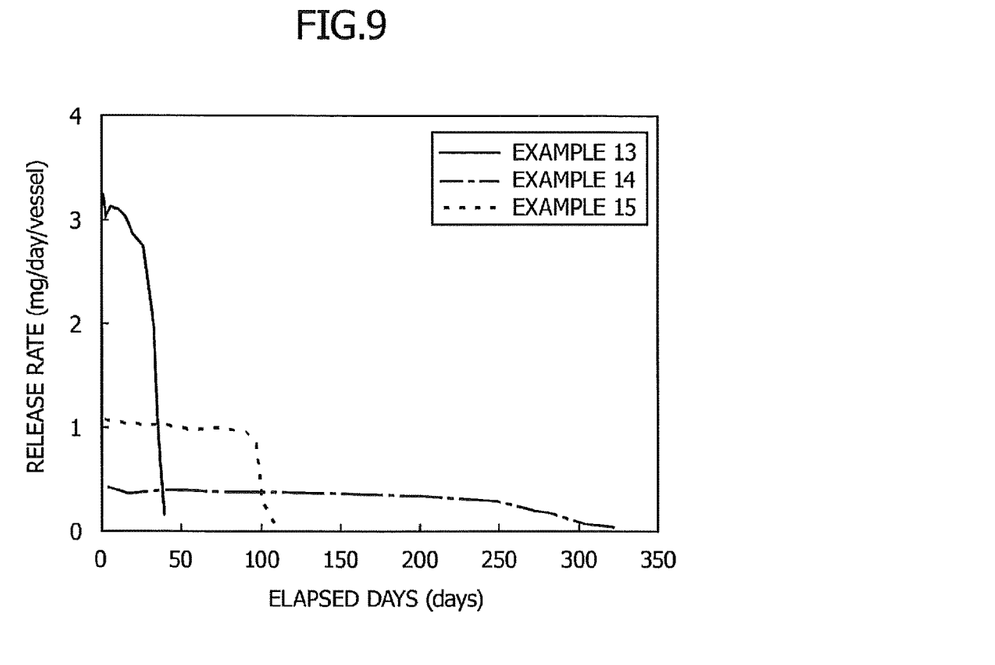
FIG. 9 is a graph showing the relationship between elapsed days and a release rate in Examples 13 to 15.

As shown in FIG. 9, the preparation thus obtained showed a stable release rate for 35 days.

Example 14

A sustained release preparation was produced and the release rate at 50° C. was determined in the same manner as in Example 8 except that 102.6 mg of 3,5-dimethyldodecanoic acid was used instead of d-limonene and 6.4 mg of dextrin palmitate ("Rheopearl KL", product of Chiba Flour Milling) was used instead of N-lauroylglutamic acid dibutylamide. The results are shown in FIG. 9.

As shown in FIG. 9, the preparation thus obtained showed a stable release rate for 250 days.

Example 15

A sustained release preparation was produced and the release rate at 50° C. was determined in the same manner as in Example 8 except that 95.8 mg of Z-11-hexadecenal was used instead of d-limonene and the amount of N-lauroylglutamic acid dibutylamide was changed to 3.4 mg. The results are shown in FIG. 9.

As shown in FIG. 9, the preparation thus obtained showed a stable release rate for 100 days.

Example 16

After 3.000 g of Z-8-dodecenyl acetate and 0.171 g of magnesium stearate were added to a cylindrical glass vessel having an inner diameter of 21 mm and an internal volume of 13.5 ml and having an opening portion with a diameter of 15 mm at the upper part of the vessel, the vessel was sealed with a lid, and heated at 80° C. for 2 minutes, the mixture to form a uniform solution. The solution was then gradually allowed to cool to room temperature. As a result, an insect pest-targeting gel composition in non-fluid form was obtained.

Figure 10:
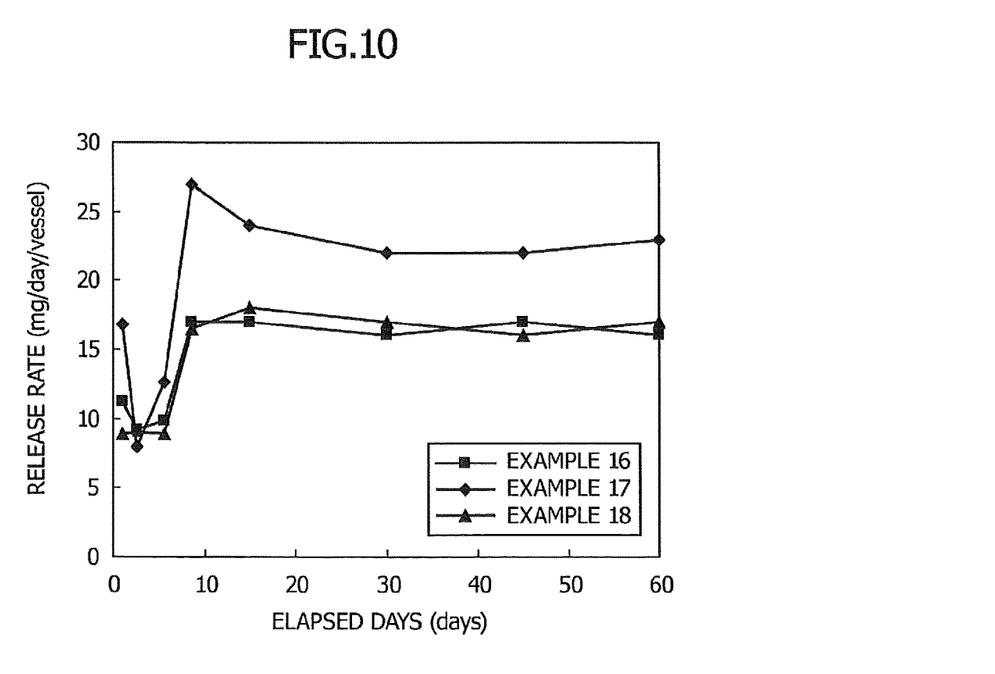
FIG. 10 is a graph showing the relationship between elapsed days and a release rate in Examples 16 to 18.

Then, the lid of the cylindrical vessel was removed, and a weight change of the volatile substance contained in the gel composition at 30° C. was measured so that the release rate was determined. The results are shown in FIG. 10.

Example 17

After 3.000 g of Z-8-dodecenyl acetate and 0.177 g of calcium stearate were added to a cylindrical glass vessel having an inner diameter of 21 mm and an internal volume of 13.5 ml and having an opening portion with a diameter of 15 mm at the upper part of the vessel, the vessel was sealed with a lid and heated at 80° C. for 2 minutes to form a uniform solution. The solution was then gradually allowed to cool to room temperature. As a result, an insect pest-targeting gel composition in non-fluid form was obtained.

Then, the lid of the cylindrical vessel was removed, and a weight change of the volatile substance contained in the gel composition was measured at 30° C. so that the release rate was determined. The results are shown in FIG. 10.

Example 18

After 3.000 g of Z-8-dodecenyl acetate and 0.249 g of aluminum stearate were added to a cylindrical glass vessel having an inner diameter of 21 mm and an internal volume of 13.5 ml and having an opening portion with a diameter of 15 mm at the upper part of the vessel, the vessel was sealed with a lid and heated at 80° C. for 2 minutes to form a uniform solution. The solution was then gradually allowed to cool to room temperature. As a result, an insect pest-targeting gel composition in non-fluid form was obtained.

Then, the lid of the cylindrical vessel was removed, and a weight change of the volatile substance contained in the gel composition was measured at 30° C. so that the release rate was determined. The results are shown in FIG. 10.

EXPLANATION OF SYMBOLS

10, 20: sustained release preparation
11, 21: insect pest-targeting gel composition
12, 22: vessel
13, 23: opening portion
13, 24: unoccupied space in the vessel
25: film

The invention claimed is:

1. An insect pest-targeting gel composition comprising:
   one or more volatile substances and
   an oil gelling agent,
wherein the one or more volatile substances are comprised in an amount of from 70.0 to 99.0% by weight by the insect pest-targeting gel composition,
wherein the oil gelling agent is selected from the group consisting of a long-chain fatty acid, a dextrin fatty acid ester, a sucrose fatty acid ester, a fructooligosaccharide fatty acid ester, a benzylidene derivative of sorbitol, and wax, and wherein the oil gelling agent is not a polyvalent metal salt of a long-chain fatty acid or 12-hydroxystearic acid.

2. The insect pest-targeting gel composition according to claim 1, wherein the one or more volatile substances are selected from the group consisting of a pheromone substance, an attractant and a repellent.

3. A sustained release preparation comprising:
   a vessel having an opening portion, and
   the insect pest-targeting gel composition as claimed in claim 1 and introduced into the vessel,
wherein the vessel is made of a material not permitting penetration of the one or more volatile substances.

4. The sustained release preparation according to claim 3, further comprising a film which covers the opening portion therewith and permits penetration of the one or more volatile substances.

5. The sustained release preparation according to claim 3, wherein the insect pest is olive fruit fly (*Bactrocera oleae*).

6. The sustained release preparation according to claim 5, wherein the volatile substance is 1,7-dioxaspiro[5.5]undecane.

* * * * *

UNITED STATES PATENT AND TRADEMARK OFFICE
CERTIFICATE OF CORRECTION

| | |
|---|---|
| PATENT NO. | : 10,244,750 B2 |
| APPLICATION NO. | : 14/362242 |
| DATED | : April 2, 2019 |
| INVENTOR(S) | : Ishibashi et al. |

Page 1 of 1

It is certified that error appears in the above-identified patent and that said Letters Patent is hereby corrected as shown below:

On the Title Page

Item (56) References Cited, FOREIGN PATENT DOCUMENTS, Column 2:
Please correct "JP 06-255124 9/1994" to read -- JP 06-256124 9/1994 --

In the Specification

Column 1, Line 48:
Please correct "JP 07-313035A11995" to read -- JP 07-313035A/1995 --

Signed and Sealed this
Twenty-third Day of July, 2019

Andrei Iancu
*Director of the United States Patent and Trademark Office*